(12) United States Patent
Di Naro

(10) Patent No.: US 10,507,165 B2
(45) Date of Patent: *Dec. 17, 2019

(54) MULTI CHAMBER FLEXIBLE BAG AND METHODS OF USING SAME

(71) Applicant: ADIENNE Pharma & Biotech SA, Lugano (CH)

(72) Inventor: Antonio Francesco Di Naro, Morcote (CH)

(73) Assignee: ADIENNE Pharma & Biotech SA, Lugano (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/249,347

(22) Filed: Jan. 16, 2019

(65) Prior Publication Data

US 2019/0142694 A1 May 16, 2019

Related U.S. Application Data

(63) Continuation-in-part of application No. 15/609,870, filed on May 31, 2017, now Pat. No. 10,369,077.

(51) Int. Cl.
*A61J 1/20* (2006.01)
*A61J 1/14* (2006.01)
(Continued)

(52) U.S. Cl.
CPC .............. *A61J 1/2024* (2015.05); *A61J 1/10* (2013.01); *A61J 1/1468* (2015.05); *A61J 1/1475* (2013.01);
(Continued)

(58) Field of Classification Search
CPC .... A61J 1/10; A61J 1/20; A61J 1/2024; A61J 1/2027; A61J 1/2093; A61J 3/00;
(Continued)

(56) References Cited

U.S. PATENT DOCUMENTS 2,435,503 A * 2/1948 Levinson ................. A23B 5/03
34/289
3,218,731 A * 11/1965 Stinchfield ................ F26B 5/06
34/242
(Continued)

FOREIGN PATENT DOCUMENTS

CN 104443822 A 3/2015
WO 2016183018 A1 11/2016

*Primary Examiner* — Kami A Bosworth
(74) *Attorney, Agent, or Firm* — Sterne, Kessler, Goldstein & Fox P.L.L.C.

(57) ABSTRACT

A method of preparing a pharmaceutical product in a single multiple chamber flexible bag. A pharmaceutical product is introduced in a liquid state into a first chamber of the flexible bag through a first port. The pharmaceutical product is lyophilized within the first chamber of the flexible bag to provide a lyophilized pharmaceutical product. The flexible bag has a second chamber and the first chamber and the second chamber are separated by a breakable seal. The second chamber further includes a reconstituting solution for reconstituting the lyophilized pharmaceutical product in the first chamber. A user may apply pressure to the flexible bag to break the seal and mix the lyophilized pharmaceutical product and the reconstituting solution to order to administer the pharmaceutical product to a patient.

11 Claims, 13 Drawing Sheets

(51) Int. Cl.

| | |
|---|---|
| *A61K 31/4184* | (2006.01) |
| *A61K 31/706* | (2006.01) |
| *A61K 45/06* | (2006.01) |
| *A61M 5/14* | (2006.01) |
| *B65D 77/04* | (2006.01) |
| *B65D 81/32* | (2006.01) |
| *A61J 1/10* | (2006.01) |
| *B65D 75/58* | (2006.01) |
| *A61K 9/19* | (2006.01) |
| *C08L 25/08* | (2006.01) |
| *F26B 5/06* | (2006.01) |
| *F26B 25/06* | (2006.01) |

(52) U.S. Cl.
CPC .......... *A61J 1/2089* (2013.01); *A61J 1/2093* (2013.01); *A61K 31/4184* (2013.01); *A61K 31/706* (2013.01); *A61K 45/06* (2013.01); *A61M 5/1407* (2013.01); *A61M 5/1411* (2013.01); *A61M 5/1413* (2013.01); *B65D 75/5883* (2013.01); *B65D 77/04* (2013.01); *B65D 81/3261* (2013.01); *B65D 81/3266* (2013.01); *B65D 81/3272* (2013.01); *A61K 9/19* (2013.01); *A61M 2205/3606* (2013.01); *C08L 25/08* (2013.01); *F26B 5/06* (2013.01); *F26B 25/063* (2013.01)

(58) Field of Classification Search
CPC .. A61J 3/02; A61J 3/10; B65D 51/241; B65D 81/3261; B65D 81/3266
See application file for complete search history.

(56) References Cited

U.S. PATENT DOCUMENTS

| | | | |
|---|---|---|---|
| 3,474,543 A * | 10/1969 | Thompson | F26B 5/06 34/287 |
| 3,756,389 A * | 9/1973 | Firth | B65D 81/3266 206/219 |
| 4,035,924 A * | 7/1977 | Faure | B65B 31/024 34/287 |
| 4,365,629 A | 12/1982 | Pert et al. | |
| 4,458,811 A | 7/1984 | Wilkinson | |
| 4,608,043 A | 8/1986 | Larkin | |
| 4,973,327 A | 11/1990 | Goodrich et al. | |
| 4,994,056 A | 2/1991 | Ikeda | |
| 4,997,083 A * | 3/1991 | Loretti | A61J 1/2093 206/219 |
| 5,114,004 A | 5/1992 | Isono et al. | |
| 5,176,634 A | 5/1993 | Smith et al. | |
| 5,309,649 A | 5/1994 | Bergmann et al. | |
| 5,385,547 A | 1/1995 | Wong et al. | |
| 5,462,526 A | 10/1995 | Barney et al. | |
| 5,501,887 A | 3/1996 | Tanaka et al. | |
| 5,853,388 A | 12/1998 | Semel | |
| 5,865,309 A | 2/1999 | Futugawa et al. | |
| 5,944,709 A * | 8/1999 | Barney | A61J 1/10 206/219 |
| 6,007,529 A * | 12/1999 | Gustafsson | A61J 1/00 604/410 |
| 6,017,598 A * | 1/2000 | Kreischer | A61J 1/10 428/35.4 |
| 6,123,696 A | 9/2000 | Coelho et al. | |
| 6,186,998 B1 | 2/2001 | Inuzuka et al. | |
| 6,319,243 B1 * | 11/2001 | Becker | A61J 1/2093 604/518 |
| 6,468,259 B1 * | 10/2002 | Loretti | B29C 66/73921 206/828 |
| 6,517,526 B1 | 2/2003 | Tamari | |
| 6,645,191 B1 | 11/2003 | Knerr et al. | |
| 6,773,425 B1 | 8/2004 | Tamari | |
| 6,814,724 B2 | 11/2004 | Taylor | |
| 6,996,951 B2 | 2/2006 | Smith | |
| 7,169,138 B2 | 1/2007 | Becker et al. | |
| 7,169,547 B2 | 1/2007 | Rubinstein et al. | |
| 7,776,022 B2 | 8/2010 | McCarthy et al. | |
| 7,658,279 B2 | 9/2010 | Oka et al. | |
| 8,096,971 B2 | 1/2012 | Bassarab et al. | |
| 8,343,128 B2 | 1/2013 | Nagao et al. | |
| 8,449,520 B2 | 5/2013 | Pepper et al. | |
| 8,863,532 B2 | 10/2014 | Voute et al. | |
| 8,979,817 B2 | 3/2015 | Chung et al. | |
| 9,278,051 B2 | 3/2016 | Inoue et al. | |
| 9,346,571 B2 | 5/2016 | Provitera | |
| 9,561,893 B2 | 2/2017 | Root et al. | |
| 9,636,297 B2 | 5/2017 | Simonnet et al. | |
| 2001/0047162 A1 | 11/2001 | Yugari | |
| 2004/0134802 A1 | 7/2004 | Inoue et al. | |
| 2005/0144804 A1 * | 7/2005 | Alstat | C02F 1/22 34/257 |
| 2005/0194060 A1 * | 9/2005 | Houwaert | A61J 1/10 141/114 |
| 2007/0029001 A1 * | 2/2007 | Trouilly | A61K 9/0019 141/114 |
| 2007/0074980 A1 | 5/2007 | Bankoski et al. | |
| 2008/0004594 A1 * | 1/2008 | Pahlberg | A61J 1/2093 604/410 |
| 2008/0255535 A1 * | 10/2008 | Yoshikawa | A61J 1/2093 604/410 |
| 2008/0268058 A1 | 10/2008 | Keenan | |
| 2010/0049156 A1 | 2/2010 | Dickhorner | |
| 2010/0290718 A1 * | 11/2010 | Laubacher | B65D 81/3266 383/38 |
| 2013/0131174 A1 | 5/2013 | Castillo | |
| 2016/0058663 A1 | 3/2016 | Kumar | |
| 2016/0000650 A1 | 7/2016 | Gobbi et al. | |
| 2017/0203871 A1 | 7/2017 | Murto et al. | |

\* cited by examiner

MULTI CHAMBER FLEXIBLE BAG AND METHODS OF USING SAME

CROSS-REFERENCE TO RELATED APPLICATIONS

This application is a continuation-in-part of U.S. patent application Ser. No. 15/609,870, filed May 31, 2017.

BACKGROUND

Field of the Invention

Embodiments of the invention generally relate to a multi chamber flexible bag for use with pharmaceutical products. More particularly, embodiments relate to methods, systems, and apparatuses for manufacturing, storing, reconstituting, diluting, and administering of lyophilized pharmaceutical products to a patient.

Background

Lyophilization or freeze-drying is a technique applied to pharmaceutical products. Through lyophilization, the shelf-life of pharmaceutical products that would have been minimal in a liquid state may be extended and standardized. Lyophilization is the process of removing the liquid portion from a frozen sample by converting the liquid portion directly into vapor without the intermediate formation of the liquid. The main steps of lyophilizing are freezing (from a liquid state to a solid state), primary drying (sublimation), and secondary drying (with high temperatures for removing the non-frozen liquid).

BRIEF SUMMARY

The following presents a simplified summary of the present disclosure in order to provide a basic understanding of some aspects described herein. This summary is not an extensive overview and is not intended to identify key or critical elements or to delineate the scope of the claims. The following summary merely presents various described aspects in a simplified form as a prelude to the more detailed description provided below.

The present embodiments relate to processes, systems, and apparatuses for lyophilizing a pharmaceutical product within a multi chamber flexible bag. The lyophilized pharmaceutical product may be stored and reconstituted within the same multi chamber flexible bag in which the pharmaceutical product was lyophilized. By lyophilizing, storing, and reconstituting the pharmaceutical product within the same bag, the bag acts a self-contained product that is ready to administer to a patient without having to include additional manipulation steps outside of the multi chamber flexible bag. The advantages of the multi chamber flexible bag are a reduction in reconstitution time and error, avoidance of accidental exposure of health care workers during dilution, reconstitution, and handling of the pharmaceutical products resulting in an increase in compliance with regulations.

Aspects of the disclosure may include a method of preparing a pharmaceutical product in a single multiple chamber flexible bag. A pharmaceutical product is introduced in a liquid state into a first chamber of the flexible bag through a first port. The pharmaceutical product is lyophilized within the first chamber of the flexible bag to provide a lyophilized pharmaceutical product. The flexible bag has a second chamber and the first chamber and the second chamber are separated by a breakable seal. The second chamber further includes a reconstituting solution for reconstituting the lyophilized pharmaceutical product in the first chamber. A user may apply pressure to the flexible bag to break the seal and mix the lyophilized pharmaceutical product and the reconstituting solution to order to administer the pharmaceutical product to a patient. Additional chambers may also be used to form the bag. For example, a third or fourth chamber may be separated from one of the first and second chambers. The third or fourth chamber may be separated by a breakable seal or other means, for example, a valve.

Another aspect of the disclosure may include a flexible pharmaceutical bag with a first chamber configured to hold a lyophilized pharmaceutical product and a second chamber separated from the first chamber. In some embodiments, the second chamber is configured to hold a reconstituting solution for reconstituting the lyophilized pharmaceutical product in the first chamber. The bag may further include a seal disposed between the first chamber and the second chamber that separates and seals the first chamber from the second chamber. A first port is attached to the first chamber, the first port configured to introduce a pharmaceutical product into the first chamber and allow passage of water vapor from the pharmaceutical product during lyophilization of the pharmaceutical product. The second chamber may include second port attached to the second chamber, the second port configured to introduce the reconstituting solution for reconstituting the lyophilized pharmaceutical product in the first chamber. A health care worker may break the seal to mix the lyophilized pharmaceutical product and the reconstituting solution. The flexible pharmaceutical bag may also include a third chamber. The third chamber may be configured to hold a solution or other product. A second seal may be disposed between the third chamber and one of the first and second chambers. Alternatively, the third chamber may be separated from one of the first and second chambers by a valve. The valve may be a one-way valve and may have a breakable seal.

In another aspect of the invention, the bag may be fabricated from a material that is able to withstand autoclave sterilization at 121° Celsius and lyophilization at −55° Celsius.

BRIEF DESCRIPTION OF THE DRAWINGS

Some features herein are illustrated by way of example, and not by way of limitation, in the accompanying drawings. In the drawings, like numerals reference similar elements between the drawings.

DETAILED DESCRIPTION

Figure 1:
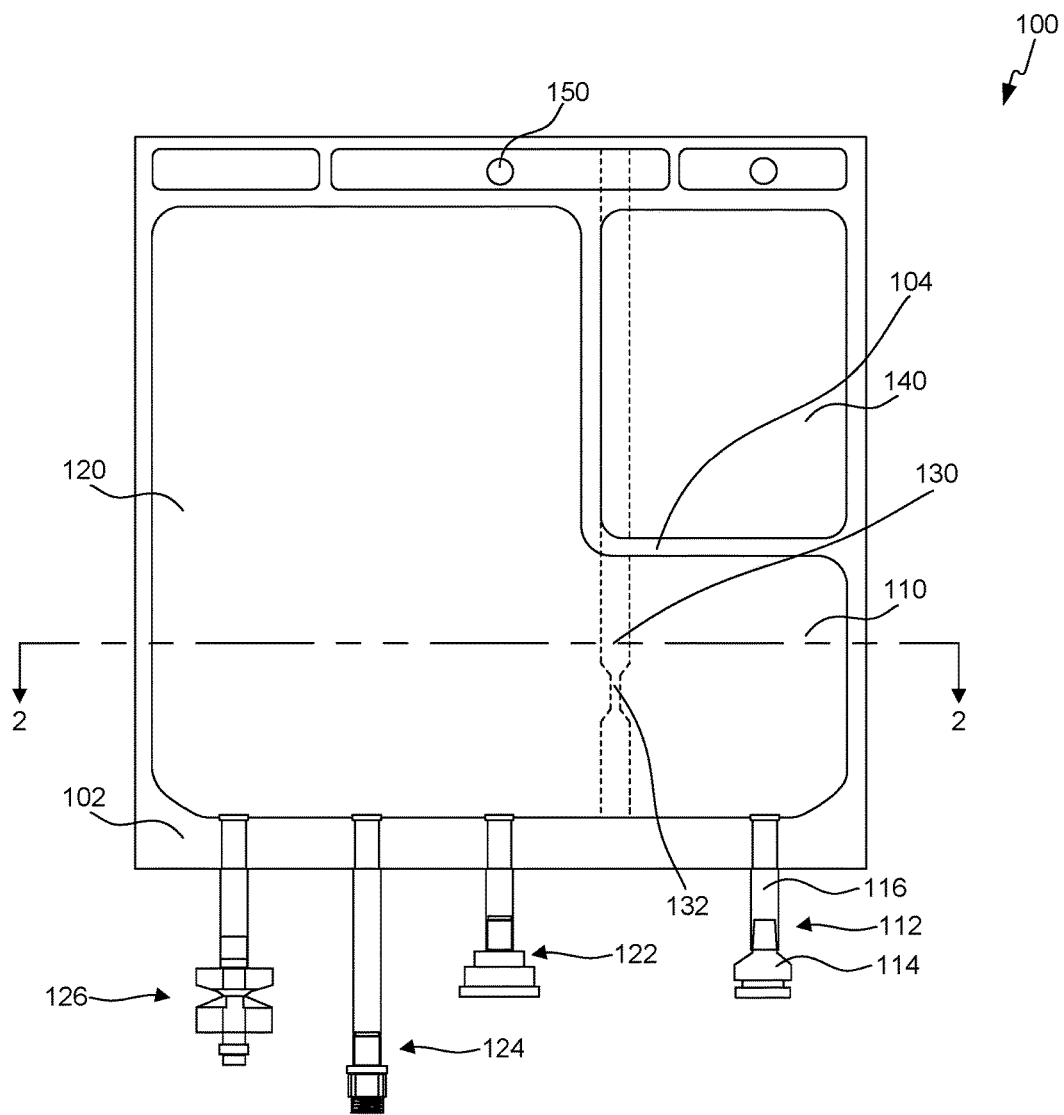
FIG. 1 illustrates a multi chamber flexible bag for holding a lyophilized pharmaceutical product and a corresponding reconstituting solution according to an embodiment.

The present inventions will now be described in detail with reference to embodiments thereof as illustrated in the accompanying drawings, in which like reference numerals are used to indicate identical or functionally similar elements. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present inventions. Other suitable modifications and adaptations of the variety of conditions and parameters normally encountered in the field, and which would be apparent to those skilled in the art, are within the spirit and scope of the inventions.

The present embodiments relate to processes, systems, and apparatuses for lyophilizing a pharmaceutical product within a multi chamber flexible bag. The lyophilized pharmaceutical product may be stored and reconstituted within the same multi chamber flexible bag in which the pharmaceutical product was lyophilized. By lyophilizing, storing, and reconstituting the pharmaceutical product within the same bag, the bag acts a self-contained product that is ready to administer to a patient without having to include additional manipulation steps outside of the multi chamber flexible bag. The advantages of the multi chamber flexible bag are a reduction in reconstitution time and error, avoidance of accidental exposure of health care workers during dilution, reconstitution, and handling of the pharmaceutical products resulting in an increase in compliance with regulations.

The multi chamber flexible bag may be used with a number of pharmaceutical products. For example, the multi chamber flexible bag may be advantageous for the preparation of cytotoxic drugs, anti-neoplastic, immunomodulatory, and/or chemotherapeutic products. Examples of cytotoxic compounds and antineoplastic compounds include at least azacytidine, belinostat, bendamustine, brentuximab vedotin, bleomycin, bortezomib, busulfan, carboplatin, carmustine, cyclophosphamide, cytarabine, dacarbazine, dactinomycin, daunorubicin, decitabine, deferoxamine, doxorubicin, epirubicin hydrochloride, fludarabine, fotemustine, fulvestrant, gemcitabine, idarubicin, ifosfamide, irinotecan hydrochloride, ixabepilone, melphalan, methotrexate, oxaliplatin, paclitaxel, pemetrexed, pentostatin, raltitrexed, romidepsin, temozolomide, thiotepa, topotecan, trabectedin, trastuzumab, and vinblastine. Cytotoxic drugs describe a group of medicines that contain chemicals which are toxic to cells, preventing their replication or growth, and are used to treat cancer and other disorders. Cytotoxic drugs are commonly manufactured in lyophilized form to extend the shelf life of the drug, ease transportation of the drugs, and for the health and well-being of heath care workers who handle and administer cytotoxic drugs to patients. The present application may also be applicable to other products that may be lyophilized such as, nutritional elements, nutraceuticals, plasma, blood products, and blood derivatives.

Other pharmaceutical products may be used with the multi chamber bag. Examples of antibiotic compounds include at least amikacin, erythromycin, and mitomycin. Examples of antimicotic compounds include at least amphotericin, anidulafungin, flucytosine, fluconazole, isavuconazonium sulfate, micafungin, rifampicin, and voriconazole. Examples of antiviral compound include at least aciclovir and ganciclovir. Examples of beta-blocking compounds include at least esmolol. Example of detoxifying compounds include at least amifostine, dexrazoxane, and levoleucovorin calcium. Example of immunomodulating compounds include at least abatacept, aldesleukin, belimumab, degarelix, infliximab, mifamurtide, and tasonermin. Examples of antibacterial compounds include at least amoxicillin, ampicillin, ampicillin/sulbactam, azithromycin, aztreonam, cefuroxime, clarithromycin, daptomycin, caspofungin, cefalotin, cefamandole, cefotaxime, cefazolin, cefepime, ceftazidime, cefoxitin, ceftobiprole medocaril, cefatoroline fosamil, chloramphenicol, dalbavancin hydrochloride, delfoprostin/quinuprostin, doripenem, ertapenem, gentamicin, imipenem/cilastatin, meropenem, oritavancin diphosphate, oxacillin, piperacillin/tazobactam, pentamidine, tedizolid phosphate, teicoplanin, telavancin hydrochloride, tigecycline, and vancomycin. Examples of anti-inflammatory compounds include at least diclofenac, ibuprofen, and indomethacin. Examples of anti-haemorrhagic compounds include at least alpha 1 antitrypsin, coagulation factor VII, coagulation factor VIII, coagulation factor IX, human anti-hemophilic prothrombin complex, gabexate, moroctocog alfa, nonacog alfa, octocog alfa, and simoctocog alfa. Examples of antiemetic compounds include at least fosaprepitant. Examples of antithrombotic compounds include at least alteplase, bivalirudin, cangrelor, epoprostenol, and urokinase. Examples of proton pumps inhibitors include at least esomeprazole, omeprazole, and pantoprazole. Examples of anxiolytics compounds include at least lorazepam. Examples of calcium channel blocker compounds include at least diltiazem. Examples of antidotes compounds include at least pralidoxime. Examples of enzymes include at least algasidase beta, alglucosidase alfa, alpha-glucosidase, beta-glucosidase, alpha-galactosidase, beta-galactosidase, taliglucerase alfa, and velaglucerase alfa. Examples of hormones include at least glucagone, levothyroxine sodium, menotrophin, somatorelin, somatostatin, somatropin, and urofollitropin. Examples of anti-neovascularization compounds include at least verteporfin. Examples of compounds for treatment of bone diseases include at least zoledronic acid. Examples of compounds for cardiac therapy include at least nesiritide. Examples of hormones for diagnostic use include at least secretin and somatorelin.

Due to the toxicity of cytotoxic drugs, occupational exposure to health care workers presents significant risks, especially when control measures are inadequate. Control measures may include the use of protective clothing, protective devices, and protective equipment to avoid accidental exposure. Health care workers may be exposed to cytotoxic drugs by inhalation, dermal contact, or orally.

Inhalation exposure may occur via droplets, particulate, and vapors when an aerosol is created. Because the molecular size of vapors is smaller than particulates, biological safety cabinets may not be able to remove the vapors from the atmosphere. Dermal exposure may occur when health care workers touch contaminated surfaces during the preparation, administration, or disposal of drugs. Contamination may be found on work surfaces situated throughout a hospital medication system (process flow of cytotoxic drugs at a facility from initial delivery to final waste disposal) and is not strictly limited to the drug preparation and drug administration areas. Oral exposure may occur from hand-to-mouth contact.

Embodiments of the current disclosure are directed to a bag that is configured to lyophilize a pharmaceutical product within a chamber of the bag. In some embodiments, the bag is configured to hold a reconstituting solution in another chamber of the bag, and allow mixing of the lyophilized pharmaceutical product with the reconstituting solution in the bag. In some embodiments, the bag is configured to allow administration of the reconstituted pharmaceutical product to a patient from the bag. In some embodiments, the bag may advantageously maintain the pharmaceutical product within the bag without additional manipulation steps of the pharmaceutical product outside of the bag after the pharmaceutical product has been introduced into the bag.

FIG. 1 illustrates an exemplary embodiment of a multi chamber flexible bag 100. While FIG. 1 illustrates bag 100 with two chambers, but the present disclosure is not so limited. Bag 100 may have multiple chambers for holding various components and solutions. Bag 100 may include an outer seal 102 that extends around the perimeter of bag 100. Outer seal 102 may provide an oxygen and water vapor seal to avoid contamination of the contents (e.g., pharmaceutical products, reconstituting solution, etc.) stored within bag 100. Outer seal 102 defines the outer limits of a first chamber 110 and a second chamber 120. In one embodiment, as shown in FIG. 1, bag 100 includes a first chamber 110 for holding and lyophilizing a pharmaceutical product. First chamber 110 may include a port 112 for introducing the pharmaceutical product into first chamber 110 in a sterile manner. Port 112 may also be used in the lyophilization procedure to enable that passage of water vapor from the pharmaceutical product. First chamber 110 may have a volume suitable for lyophilizing a pharmaceutical product. For example, first chamber 110 may have a volume of 50 ml. Other suitable volumes may be used.

Bag 100 may further include a second chamber 120 for holding a reconstituting solution or solvent. Second chamber 120 may include one or more ports for introducing the reconstituting solution into second chamber 120 and for administrating the reconstituted pharmaceutical product to a patient. For example, port 122 may be used for introducing the reconstituting solution into second chamber 120 in a sterile manner. Second chamber 120 may further include multiple administration ports 124 and 126. The types of ports 124 and 126 attached to second chamber 120 may be based on patient or health care worker preference. In operation, for example, administration ports 124 and 126 may be used by a health care worker to administer the reconstituted pharmaceutical product to a patient, for example by intravenous therapy. In another example, port 124 may attach to standard IV equipment. The dose of the reconstituted pharmaceutical product may be based on specific characteristics of the patient. For example, the body weight of the patient may be considered when adjusting the dose before the reconstituted pharmaceutical product is administered to the patient through port 126. As will be contemplated, bag 100 may be used by any suitable individual, however, for simplicity, the disclosure will refer to users as health care workers. In one embodiment, second chamber 120 may be sized relative to first chamber 110 in order to provide sufficient volume of reconstituting solution to reconstitute the pharmaceutical product in first chamber 110. In one embodiment, second chamber 120 may have a volume greater than the volume of first chamber 110. For example, second chamber 120 may have a volume of 500 ml. Other suitable volumes may be used.

Figure 5:
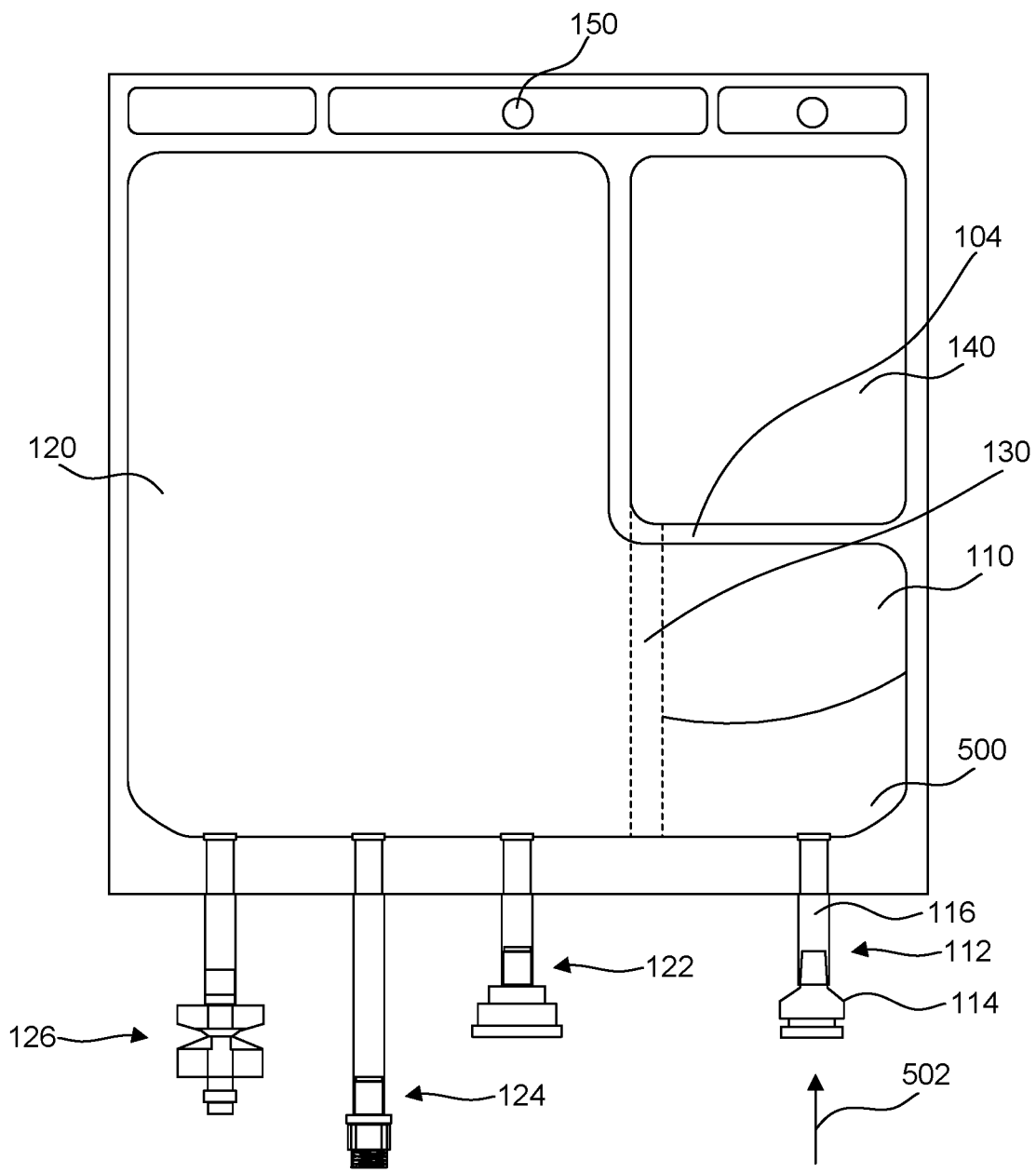
FIG. 5 illustrates a multi chamber flexible bag with a pharmaceutical product in a first chamber of the multi chamber flexible bag according to an embodiment.
Figure 6:
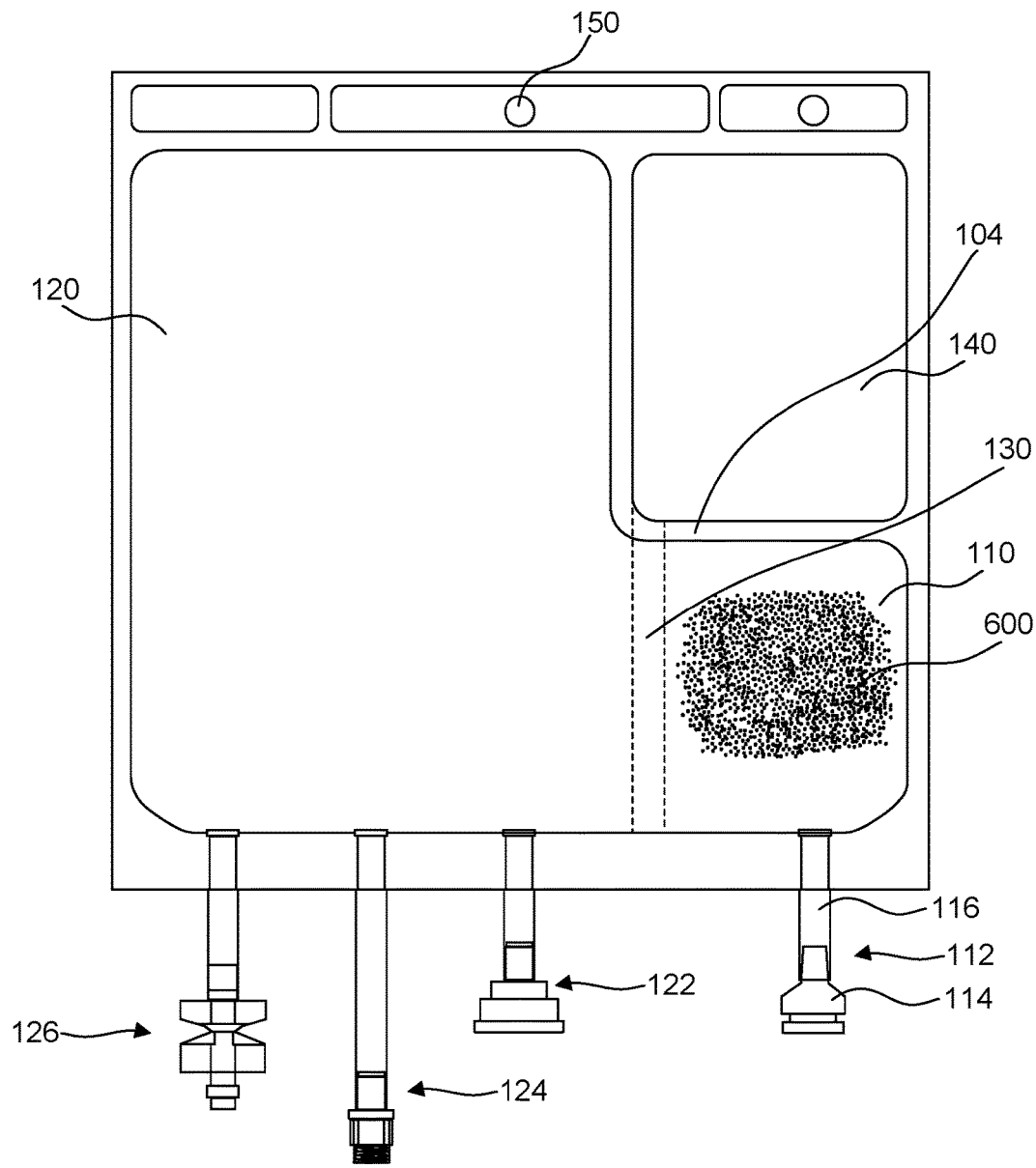
FIG. 6 illustrates a multi chamber flexible bag with a lyophilized (freeze-dried) pharmaceutical product in a first chamber of the multi chamber flexible bag according to an embodiment.
Figure 7:
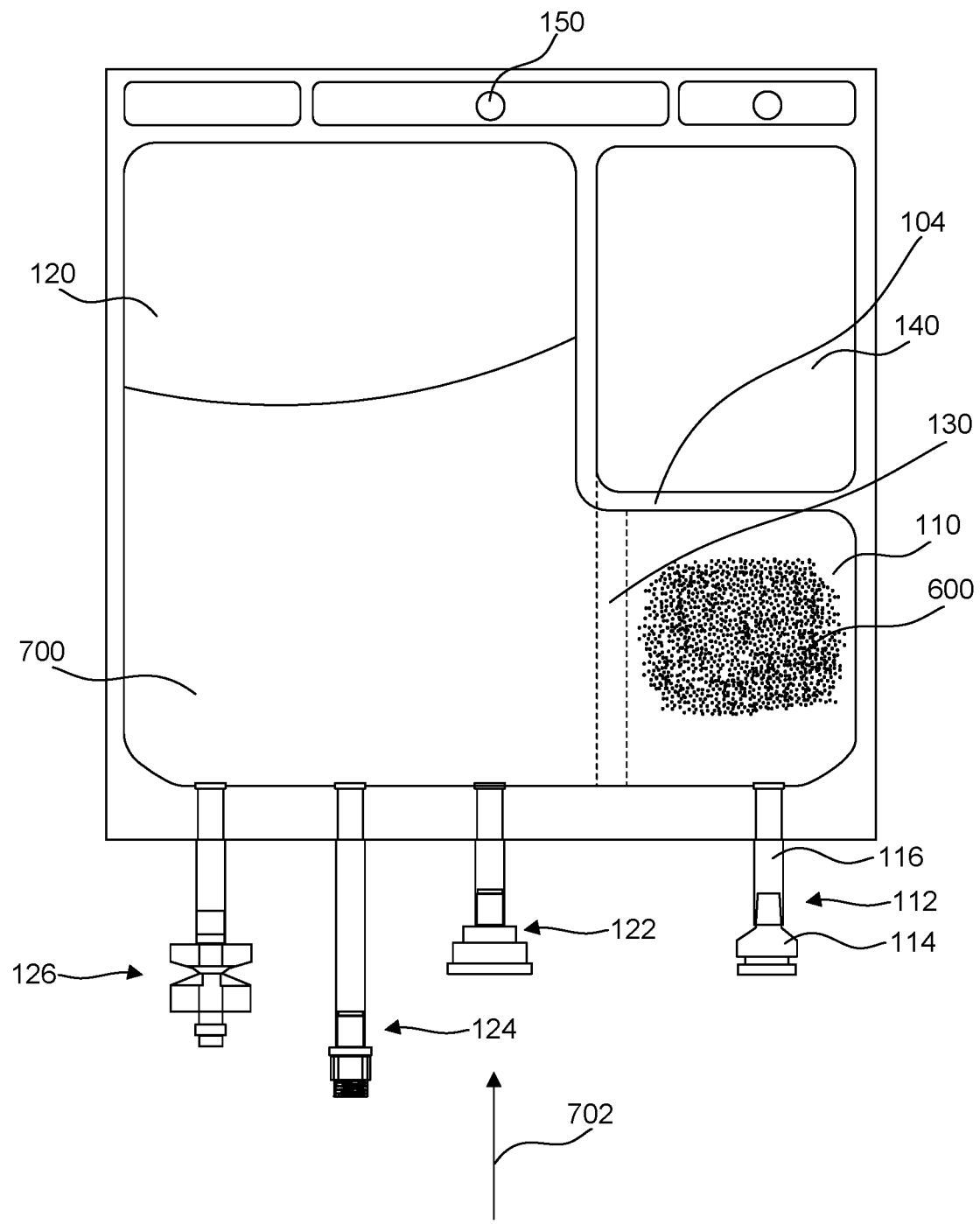
FIG. 7 illustrates a multi chamber flexible bag with a lyophilized (freeze-dried) pharmaceutical product in a first chamber of the multi chamber flexible bag and a reconstituting solution in a second chamber of the multi chamber flexible bag according to an embodiment.

Bag 100 may further include a seal 130 that separates and defines first chamber 110 and second chamber 120. Seal 130 maintains the integrity of the lyophilized pharmaceutical product and the reconstituting solution and prevents the unintended passage of the reconstituting solution to the lyophilized pharmaceutical product, or vice versa, before an appropriate time. FIG. 1 illustrates seal 130 as extending the length of bag 100, from a top of bag 100 to a bottom of bag 100. Alternatively, seal 130 may only extend a portion of the length of bag 100. In one embodiment, for example, as shown in FIGS. 5-7, seal 130 may extend from outer seal 102 of bag 100 to an inner seal 104. However, the geometry of seal 130 is not so limited. In another embodiment, seal 130 may be curved.

Figure 2:
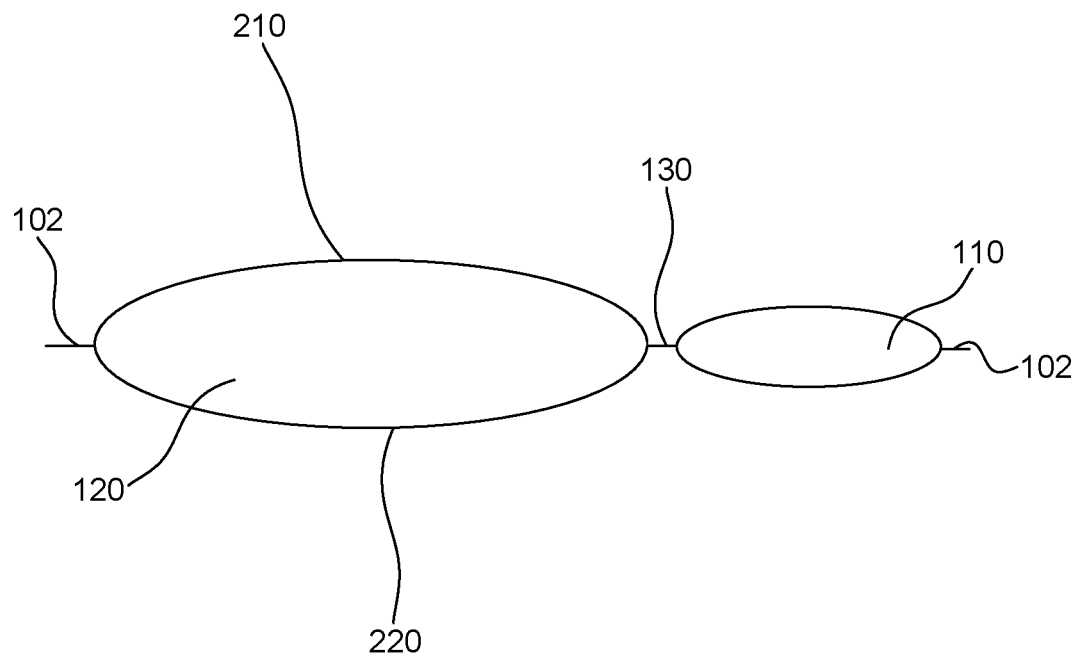
FIG. 2 illustrates a cross-sectional view of the multi chamber flexible bag taken along cross-sectional line 2-2 of FIG. 1 according to an embodiment.

In one embodiment, bag 100 may be fabricated from a tubular film or cut as a double wound film at a desired width. As shown, for example, in FIG. 2, bag 100 may include a front film 210 and a back film 220 that are joined together. Front film 210 and back film 220 may be joined together at the edges to create outer seal 102. Outer seal 102 may be created by using a predetermined temperature and a predetermined amount of pressure to seal front film 210 and back film 220. Outer seal 102 is made such that it is not breakable, at least during normal operation. In addition, front film 210 and back film 220 may be joined together within outer seal 102 to define seal 130. Seal 130 is created by using a predetermined temperature and a predetermined amount of pressure to seal front film 210 and back film 220. In this manner, seal 130 may define a connection between front film 210 and back film 220. Seal 130 is created to be breakable. Front film 210 and back film 220 may be joined together through heat sealing, RF welding, molding, and other suitable techniques. FIG. 2 illustrates a cross-sectional view of bag 100 along cross-sectional line 2-2 of FIG. 1. Cross-sectional line 2-2 intersects outer seal 102, first chamber 110, seal 130, and second chamber 120.

In one embodiment, seal 130 may be fabricated from the same material of the overall bag 100 (e.g., front film 210 and back film 220). Because bag 100 and seal 130 are fabricated from the same material, no other material comes in contact with the pharmaceutical product in order to avoid contamination. Seal 130 may be placed in various locations on bag 100 to form at least two chambers within bag 100. If bag 100 includes additional chambers, bag 100 may include additional seals to separate the chambers and define their geometry. Seal 130 may be broken by applying a predetermined amount of pressure to bag 100. For example, pressure may be applied to second chamber 120 by the health care worker's hand. The amount of pressure to break seal 130 may range from 30-70 Kgf. In this manner, seal 130 is a breakable seal. The pressure may be applied by a health care worker when the health care worker is ready to administer the pharmaceutical product to the patient, in order to extend the shelf life of the lyophilized pharmaceutical product, as shown for example in FIG. 8. Once seal 130 has been broken, the reconstituting solution mixes with the freeze-dried pharmaceutical product to produce a reconstituted pharmaceutical product. Seal 130 may have a width between 5 to 15 mm or 8 and 12 mm. Seal 130 is stronger as the width of seal 130 increases and requires more pressure to break seal 130. Seal 130 is designed to withstand a predetermined amount of pressure before breaking. For example, during transport of the flexible bag, seal 130 may undergo pressure and/or force during normal transport procedures. Seal 130 is designed to maintain its integrity under smaller amounts of pressure (e.g., less than 30 Kgf) so seal 130 does not break during transport until a predetermined amount of pressure is applied.

Seal 130 may be joined in such a way as to create a weak point 132 in seal 130 so that weak point 132 breaks first when pressure is applied to bag 100. Seal 130 may include multiple weak points 132 along the length of seal 130. Weak point 132 may have a width smaller than the rest of seal 130. For example, weak point 132 may have a width of 5 to 8 mm.

In one embodiment, seal 130 may include a valve between first chamber 110 and second chamber 120 to prevent the passage of reconstituting solution until the health care worker is ready to administer the pharmaceutical product.

Bag 100 may be fabricated from a material that provides an oxygen and water vapor barrier. The material may also be capable of withstanding the extreme temperatures of autoclave sterilization and lyophilizing. For example, the material for bag 100 is capable of withstanding autoclave sterilization at 121° Celsius and freeze dying at −55° Celsius without the material breaking down and leaching into the pharmaceutical product and reconstituting solution within the bag. The material for the bag 100 is capable of withstanding extreme temperature up to −80° Celsius. Other aspects of the material may include flexibility so that bag 100 is shatter-proof and is easy to transport. The material may also be transparent so that the health care worker may easily see within bag 100 to identify that lyophilizing and reconstitution has occurred, and see how much reconstituted pharmaceutical product is still in bag 100 during administration of the pharmaceutical product.

In one embodiment, bag 100 comprises polyolefin/styrene-block copolymer based film. The material used for bag 100 meets all of the requirements required by the United States and European pharmaceutical regulation, SFDA Standard for "Registration standard for imported pharmaceutical packaging materials" (China), International Standard ISO 15747 "Plastics containers for intravenous injection", and International Standard ISO 10993 "Biological Evaluation of medical devices."

Ports 112, 122, 124, and 126 may each include a connector 114 and a tube 116. Connectors 114 enable the sealing of ports 112, 122, 124, and 126 and enable health care workers and/or the manufacture to attach equipment for introducing solutions into the chamber and for extracting solutions from the chamber. A variety of different types of connectors 114 may be used to expand the type of equipment that may be utilized with connectors 114. Tubes 116 enable the passage of liquid or gas from the outside environment to the chambers, or vice versa. Tubes may be fabricated from a polyolefin/styrene block copolymer that is coextruded at a desired dimension. Tubes may also be fabricated from any other suitable material. Connections may be fabricated from polypropylene and polycarbonate or any other suitable material. Ports 112, 122, 124, and 126 are capable of withstanding autoclave sterilization at 121° Celsius and freeze dying at −55° Celsius or up to −80° Celsius. The outer diameter of tubes may be 8.1 mm+0.08 mm and the tube thickness may be 1.0 mm+0.08 mm. In one embodiment, the material used for ports 112, 122, 124, and 126 meets all of the requirements required by the United States and European pharmaceutical regulation, SFDA Standard for "Registration standard for imported pharmaceutical packaging materials" (China), International Standard ISO 15747 "Plastics containers for intravenous injection", and International Standard ISO 10993 "Biological Evaluation of medical devices."

Bag 100 may further include a label area 140 that is used for providing accessible information on bag 100, such as, for example, the necessary information as may be required by law. In addition, the label area 140 may include barcodes, QR codes, RFIDs, etc. for easy identification of the pharmaceutical product, dosage details, warnings, possible adverse reactions, patient information, etc.

Bag 100 may further include a through hole 150 in outer seal 102. Through hole 150 may be utilized by the health care worker to attached bag 100 to an IV stand for ease of administering the reconstituted pharmaceutical product to a patient.

Figure 3:
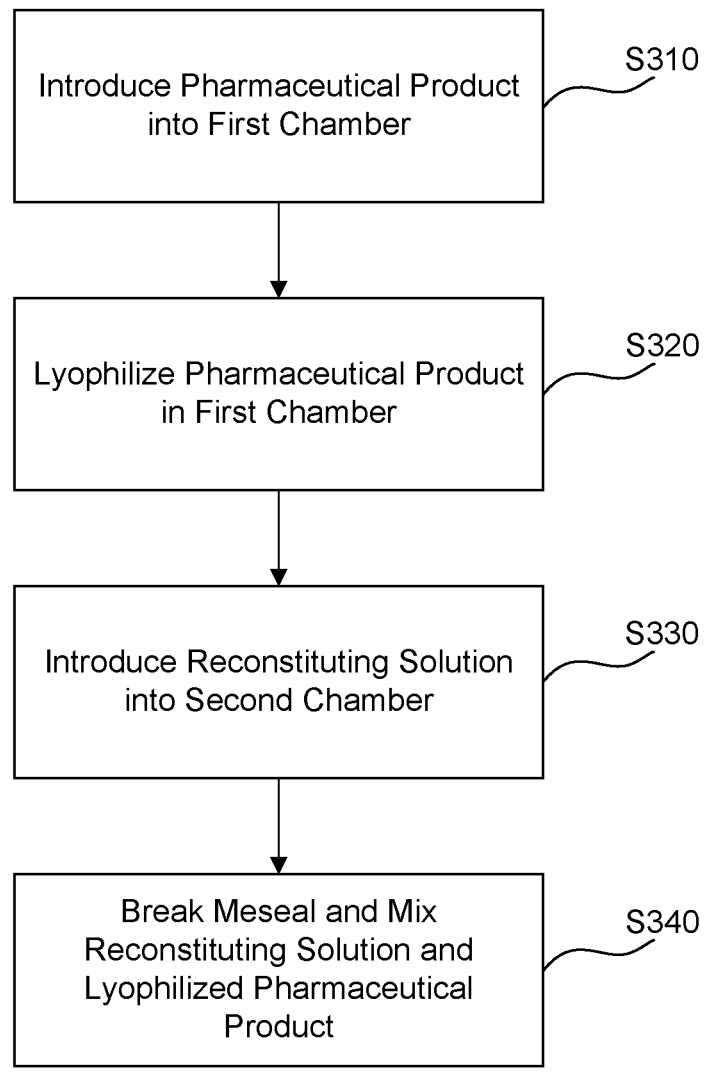
FIG. 3 illustrates a flowchart of a method for preparing a pharmaceutical product in a multi chamber flexible bag according to an embodiment.

FIG. 3 illustrates a flowchart for a method of preparing the pharmaceutical product with a single bag 100, according to an embodiment. The method includes the steps of S310 introducing the pharmaceutical product into first chamber 110, S320 lyophilizing pharmaceutical product in first chamber 110, S330 introducing reconstituting solution into second chamber 120, and S340 breaking seal 130 and mixing reconstituting solution and lyophilized pharmaceutical product. Each step will be explained in further detail below.

In step S310, a predetermined amount of the pharmaceutical product 500 of a known concentration is introduced into first chamber 110 of bag 100 through port 112 in a sterile manner. For example, pharmaceutical product may pass through a sterile filter. The amount and concentration of the pharmaceutical product is needed for calculating the dilution and reconstitution of the pharmaceutical product after lyophilization. FIG. 5 illustrates the pharmaceutical product 500 in first chamber 110. Arrow 502 indicates the passage of pharmaceutical product 500 through port 112. Pharmaceutical product 500 may comprise a liquid state. Once the pharmaceutical product 500 is within first chamber 110, port 112 is closed with a sterile stopper and bag 100 may be placed in a lyophilizer. Sterile stopper does not completely close port 112 but leaves the necessary space to permit the passage of vapor during the lyophilization process. Bag 100 is configured to withstand the conditions of lyophilizer (e.g., temperature, pressure, etc.).

In step S320, bag 100, along with other bags that also contain pharmaceutical product 500 as necessary, are placed on a tray within the lyophilizer. Bag 100 may be oriented in a vertical, or slightly angled vertical position, with port 112 at the top and the bottom of bag 100 may be secured to the tray. With port 112 at the top, port 112 enables that passage of water vapor from the pharmaceutical product during the lyophilization procedure and avoids spillage of the pharmaceutical product during lyophilization. When all of the bags are in a secure position, the freeze-drying process may begin. Table 1, provided below, provides data related to an exemplary lyophilization process for freeze-drying the pharmaceutical product. The temperatures, time, and pressures may vary in accordance with the type of pharmaceutical product placed in bag 100. FIG. 6 illustrates a bag 100 with the lyophilized pharmaceutical product 600 after the lyophilization process is complete.

TABLE 1

| | Temperature | Time (hour:minute) | Pressure |
|---|---|---|---|
| Freezing - shelves cooling | −50° C.--−42° C. | 2:00 | atm |
| Freezing - shelves holding | −50° C.--−42° C. | 6:00 | |
| Primary drying (shelves heating) | −5° C. | 10:00 | 50-400 µbar |
| Primary drying (shelves holding) | −5° C. | 20:00 | |
| Secondary drying (shelves heating) | 10° C. | 10:00 | |
| Secondary drying (shelves holding) | 10° C. | 6:00 | |
| Secondary drying (shelves heating) | 15° C. | 1:00 | |
| Secondary drying (shelves holding) | 15° C. | 10:00 | |

In S330, a predetermined amount of a sterile reconstituting solution is aseptically introduced into second chamber 120 through port 122. The amount of reconstituting solution introduced into second chamber 120 is dependent on the desired dilution of pharmaceutical product 500 for administration to a patient. FIG. 7 illustrates reconstituting solution 700 in second chamber 120. Arrow 702 indicates the passage of reconstituting solution 700 through port 122. Reconstituting solution 700 may be a sterile 0.9% saline solution, or any other suitable solution for reconstitution and dilution of pharmaceutical product 500. Other examples of reconstituting solution include water, alcohol-based solutions, etc. Examples of dilution solutions include saline solution, glucose solution, Ringer solution, etc.

In one embodiment, step S330 may be performed when bag 100 is in a plurality of different locations. For example, bag 100 may be removed from the lyophilizer and reconstituting solution 700 may be introduced in second chamber at a preparation facility and then stored and transported under refrigerated and sterile conditions.

Figure 8:
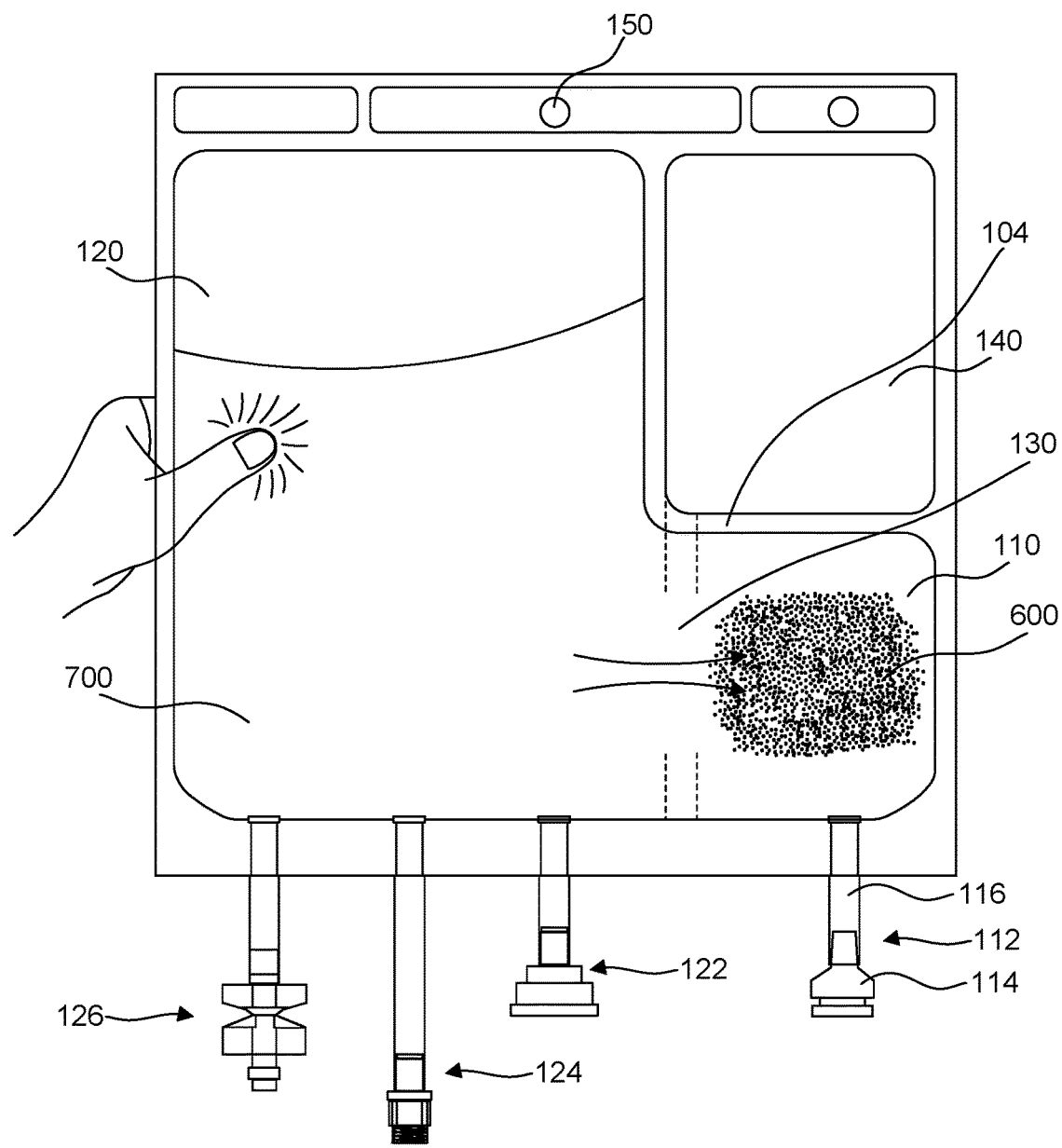
FIG. 8 illustrates a multi chamber flexible bag with a lyophilized (freeze-dried) pharmaceutical product in a first chamber of the multi chamber flexible bag and a reconstituting solution in a second chamber of the multi chamber flexible bag with pressure applied to the second chamber to break a seal in order to mix the lyophilized pharmaceutical product and the reconstituting solution according to an embodiment.

In S340, a health care worker may mix the reconstitution solution 700 with lyophilized pharmaceutical product 600 to reconstitute and properly dilute lyophilized pharmaceutical product 600 to a reconstituted pharmaceutical product 900. The health care worker may break seal 130 by applying pressure by hand to bag 100, for example to second chamber 120, which is illustrated in FIG. 8. Because bag 100 is flexible, when the health care worker presses on the bag, pressure is created within bag 100 and is applied to seals 102, 104, and 130. Outer seal 102 and inner seal 104 are stronger than seal 130 that separates first chamber 110 and second chamber 120 so that seal 130 breaks before outer seal 102 and inner seal 104.

When a predetermined amount of pressure (e.g., 30-70 kgf) is applied bag 100, seal 130 breaks and first chamber 110 and second chamber 120 become a single chamber for mixing lyophilized pharmaceutical product 600 with reconstituting solution 700. In one embodiment, the health care worker may produce more pressure by applying pressure on second chamber 120 rather than first chamber 110 because second chamber contains a liquid and first chamber 110 contains a lyophilized product and a gas. In addition, seal 130 may include weak point 132 to initiate the breaking of seal 130.

Figure 4:
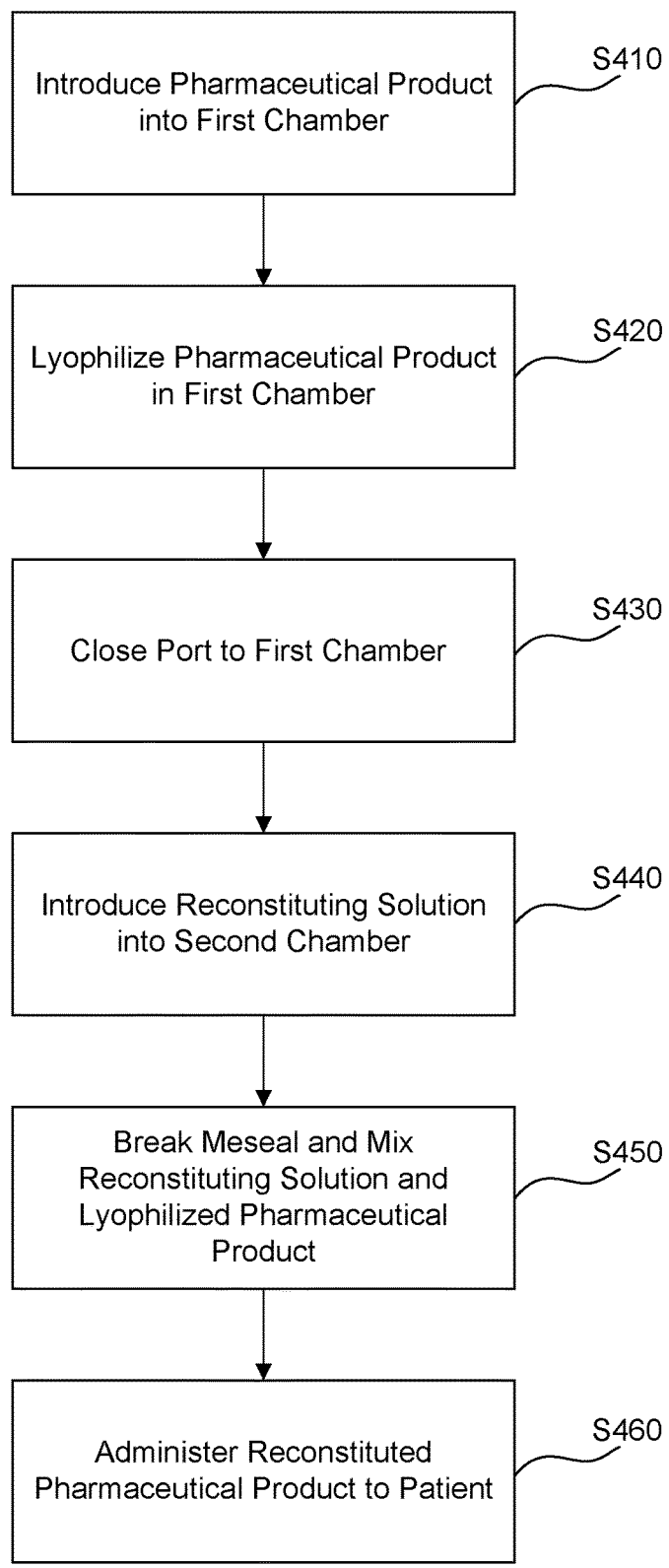
FIG. 4 illustrates a flowchart of a method for preparing a pharmaceutical product in a multi chamber flexible bag according to an embodiment.

FIG. 4 illustrates another exemplary flowchart for a method of preparing the pharmaceutical product with a single bag 100. The method includes the steps of S410 introducing the pharmaceutical product into first chamber 110, S420 lyophilizing pharmaceutical product in first chamber 110, S430, closing port 112 to first chamber 110, S440 introducing reconstituting solution into second chamber 120, S450 breaking seal 130 and mixing reconstituting solution and lyophilized pharmaceutical product, and S460 administering reconstituted pharmaceutical product to patient. Each step will be explained in further detail below.

Steps S410, S420, S440, and S450 are similar to steps S310, S320, S330, and S340 as explained above in regard to the method in FIG. 3. In S430, once the pharmaceutical product 500 is lyophilized, port 112 may be permanently closed to maintain the integrity of lyophilized pharmaceutical product 600. For example, the outside environment, e.g., oxygen, water vapor, etc., may contaminate lyophilized pharmaceutical product 600, so sealing first chamber 110 helps maintain the integrity of lyophilized pharmaceutical product 600. Port 112 may be sealed after insufflation of sterile gas. The lyophilization vacuum may be broken by an insufflation of sterile gas under slight vacuum and the gas is introduced into first chamber 110. In one embodiment, the insufflation gas is nitrogen. If the pharmaceutical product is not sensitive to oxygen, compressed air may be used as the insufflation gas. This process maintains the sterility of first chamber 110 and avoids the oxidation of lyophilized pharmaceutical product 600.

Figure 9:
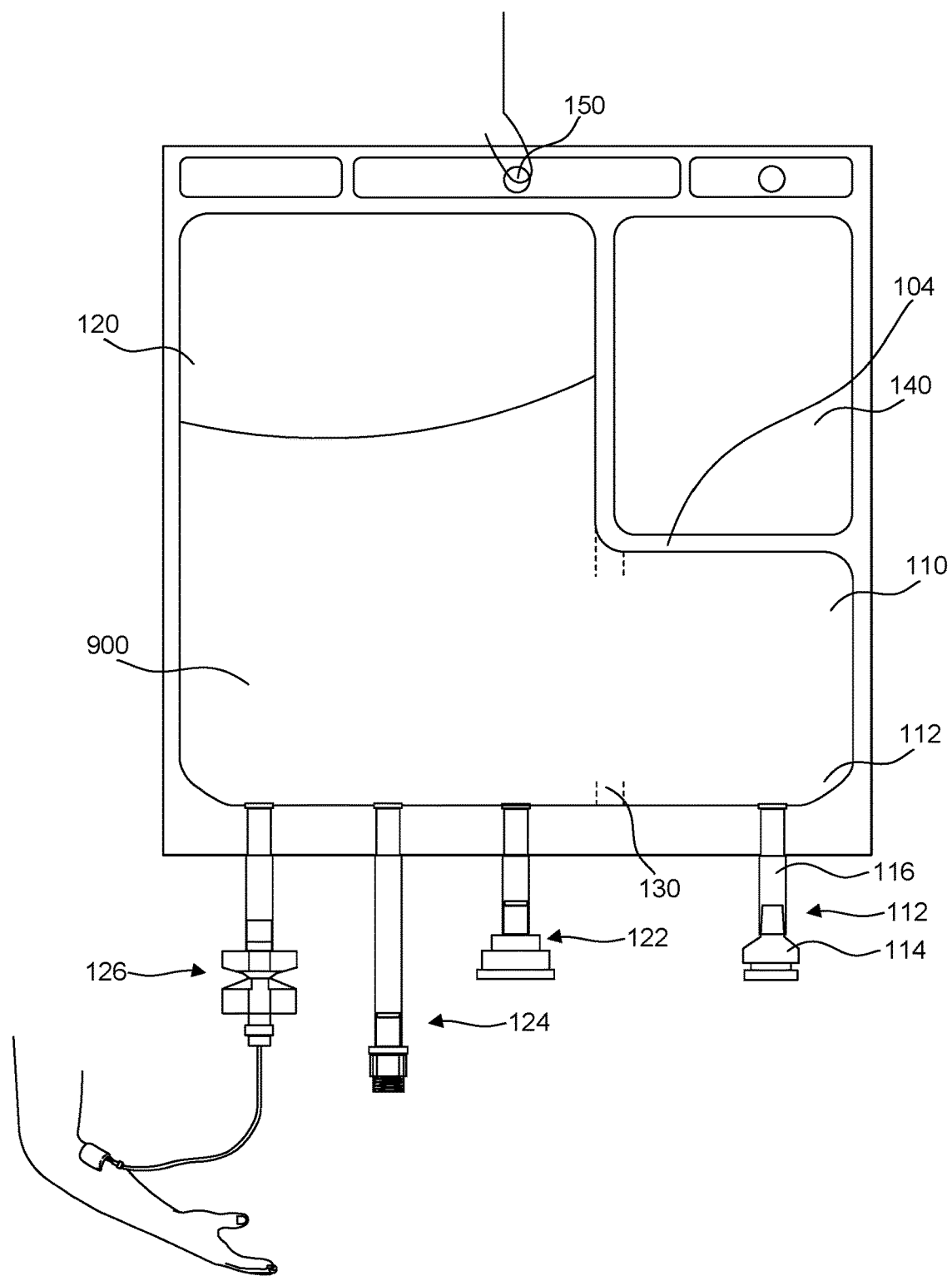
FIG. 9 illustrates a multi chamber flexible bag with a reconstituted pharmaceutical product in operation according to an embodiment.

In S460, after the health care worker has reconstituted the pharmaceutical product 900, the health care worker may administer reconstituted pharmaceutical product 900 to a patient. Reconstituted pharmaceutical product 900 may be administered in a number of ways. For example, FIG. 9 illustrates reconstituted pharmaceutical product 900 being administered by way of intravenous therapy. Through hole 150 in bag 100 allows the health care worker to hang bag 100 from an IV stand and administration ports 124 and 126 allow a health care worker attached standard IV equipment for treatment.

In addition, bag 100 may be sterilized in an autoclave at the manufacturing facility of the pharmaceutical product. The material of bag 100 enables bag 100 to withstand autoclave sterilization at 121° Celsius.

Figure 10:
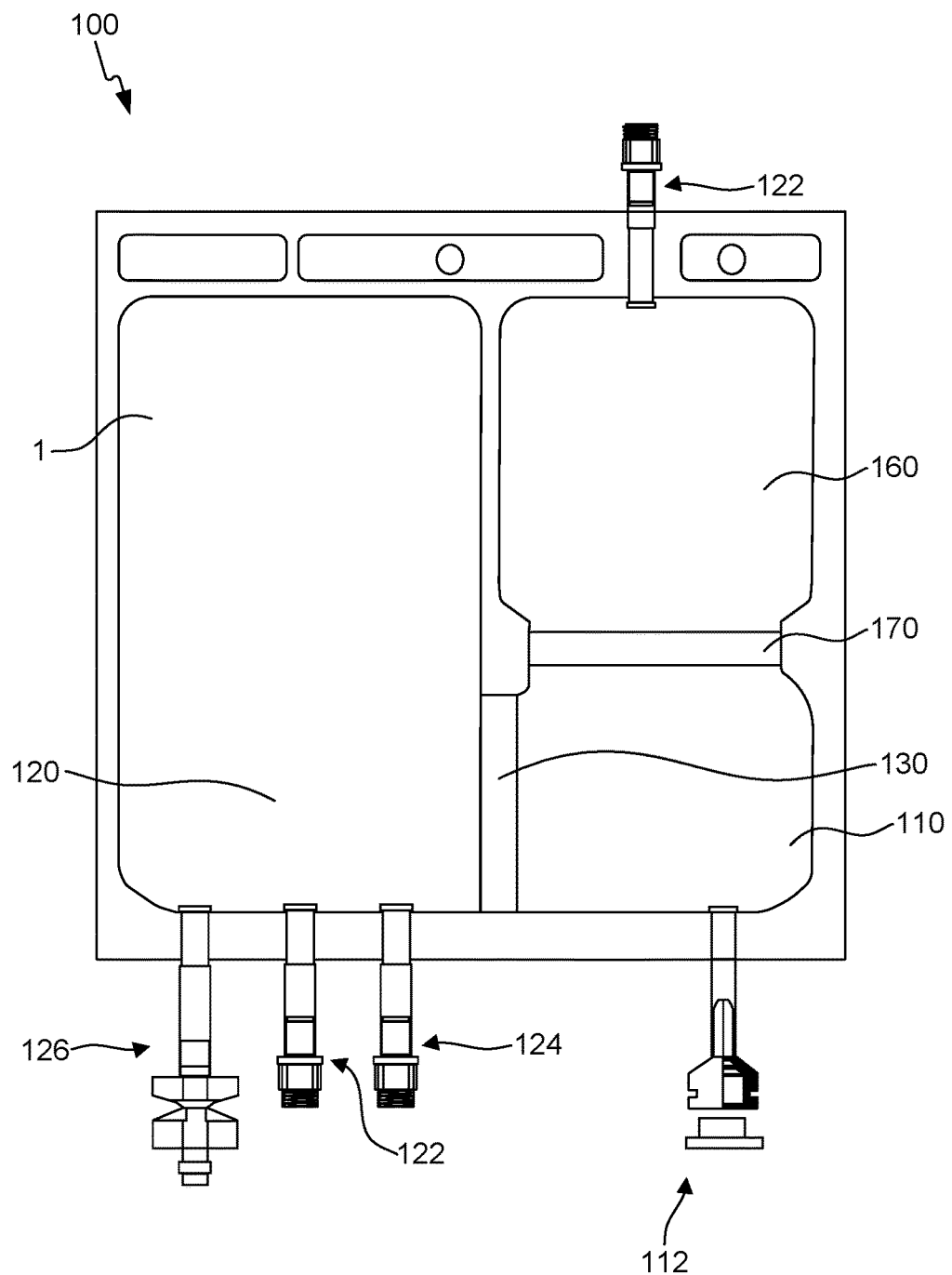
FIG. 10 illustrates a multi chamber flexible bag for holding a lyophilized pharmaceutical product according to an embodiment.

FIG. 10 shows bag 100 according to some embodiments. Bag 100 has first chamber 110 and second chamber 120. Additionally, bag 100 has a third chamber 160. Bag 100 may have more than three chambers. For example, bag 100 may have four, five, or six chambers. FIG. 10 shows breakable seal 130 separating first chamber 110 from second chamber 120. A second breakable seal 170 separates first chamber 120 from third chamber 160. In some embodiments, third chamber 160 is configured to hold another pharmaceutical product, saline solution, alcoholic solvent, or other products.

Figure 11:
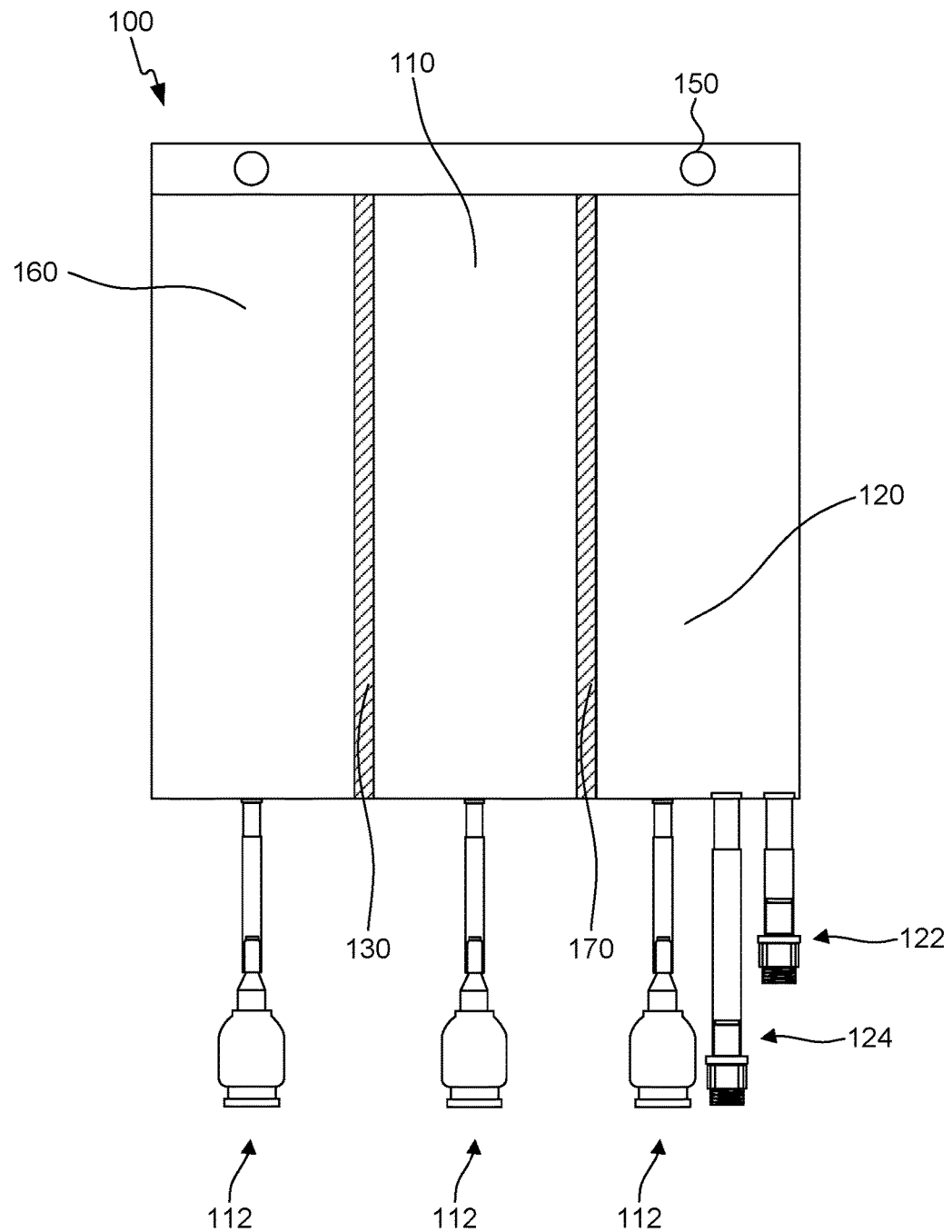
FIG. 11 illustrates a multi chamber flexible bag for holding a lyophilized pharmaceutical product according to an embodiment.
Figure 12:
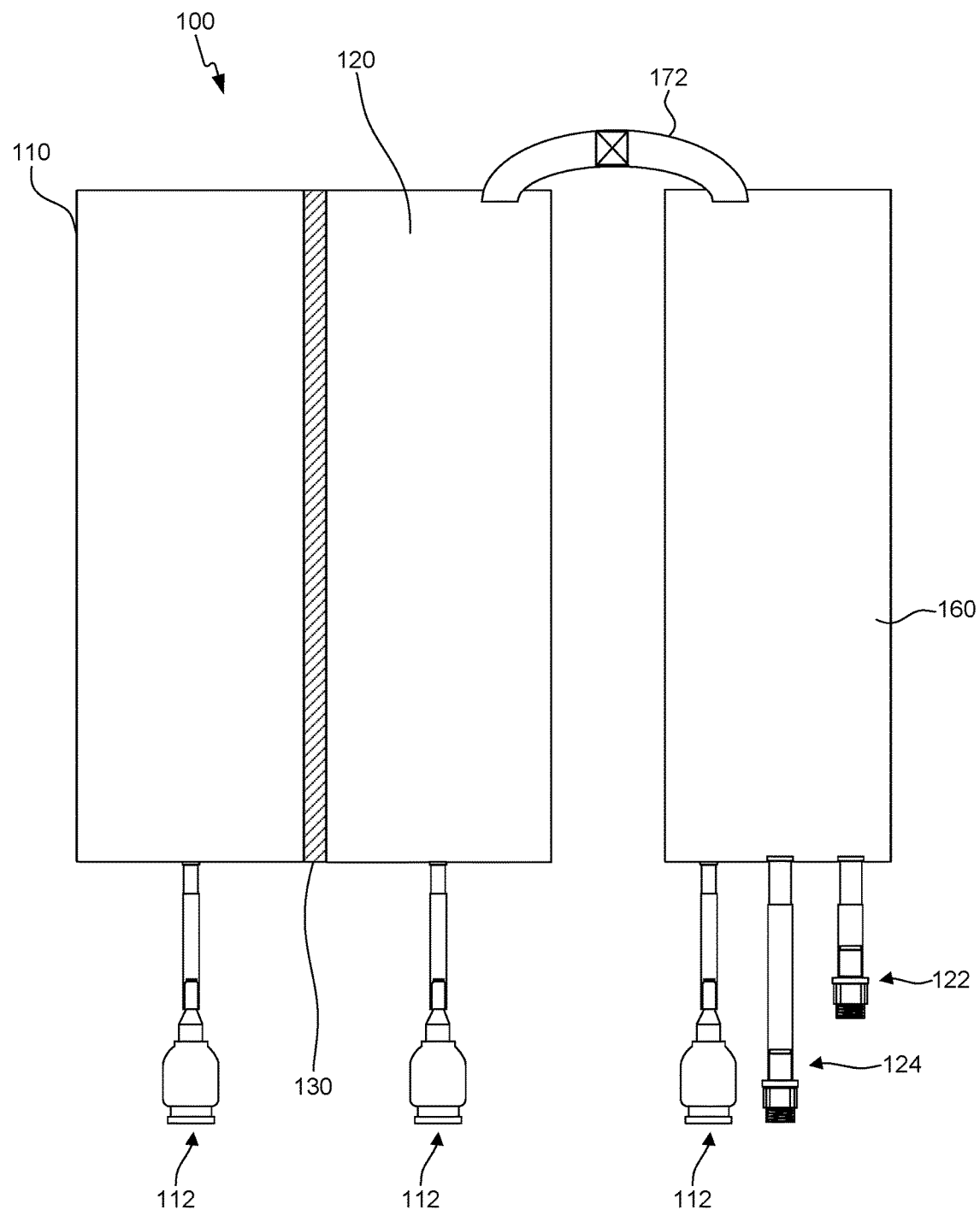
FIG. 12 illustrates a multi chamber flexible bag for holding a lyophilized pharmaceutical product according to an embodiment.
Figure 13:
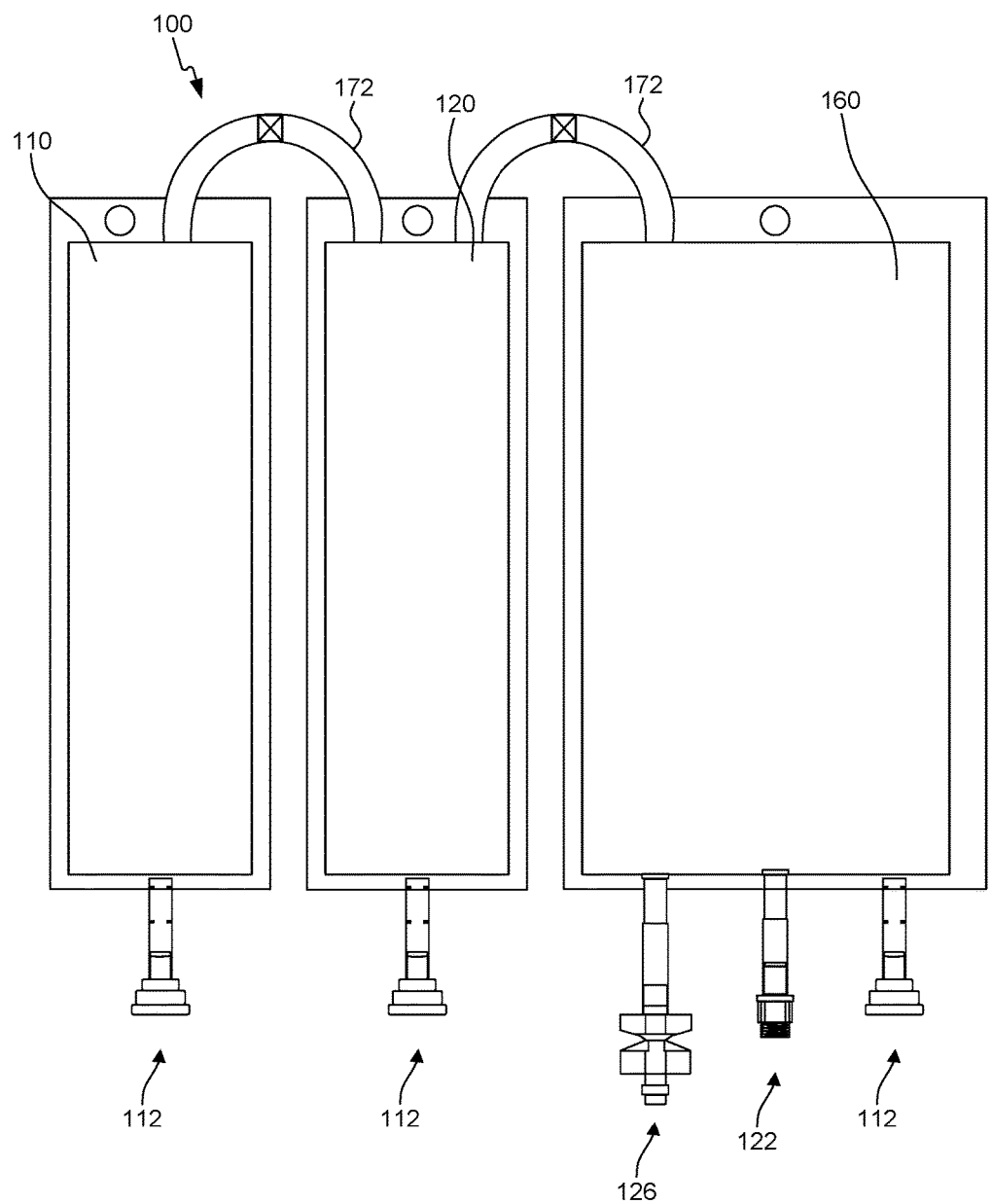
FIG. 13 illustrates a multi chamber flexible bag for holding a lyophilized pharmaceutical product according to an embodiment.

FIG. 11 shows bag 100 according to some embodiments. Bag 100 has three chambers: first chamber 110, second chamber 120, and third chamber 160. Each chamber is separated by breakable seals 130, 170 from an adjacent chamber. FIG. 12 shows bag 100 according to some embodiments. As shown in FIG. 12, a port 172 may connect chambers of bag 100. For example, as shown in FIG. 12, port 172 connects second chamber 120 and third chamber 160. Port 172 may be a valve, for example a one-way valve. In some embodiments port 172 may have a breakable valve that permanently opens in response to a pressure differential between the chambers. FIG. 13 shows bag 100 according to some embodiments. As shown in FIG. 13, a port 172 may connect chambers of bag 100. In this and other embodiments, there is no breakable seal as all chambers are connected by ports 172.

The method of lyophilizing, storing, and reconstituting a pharmaceutical product within the same flexible bag may have one or more benefits. For example, bag 100 is a ready-to-administer product that needs little manipulation by the health care worker. The pharmaceutical product is lyophilized which increases the shelf life of the pharmaceutical product. The reconstituting solution is stored in the second chamber which is prepared for the proper dilution and reconstitution of the pharmaceutical product avoiding possible reconstitution and dilution calculation errors. Additional manipulation of the pharmaceutical product outside the bag is avoided because the pharmaceutical product stays within the bag after it is introduced until the pharmaceutical product is administered. Additional manipulation introduces the possibility of product contamination and/or safety issues for health care workers, especially if the pharmaceutical product is a toxic drug, such as a cytotoxic drug. Possible contamination of the pharmaceutical product is avoided by keeping the pharmaceutical product within a single bag and sealing the first chamber from the outside environment.

Embodiments of the invention may be directed to a method of preparing a pharmaceutical product in a multiple chamber flexible bag. The method including introducing a pharmaceutical product in a liquid state into a first chamber of the flexible bag through a first port and lyophilizing the pharmaceutical product within the first chamber of the flexible bag to provide a lyophilized pharmaceutical product, wherein the flexible bag has a second chamber and the first chamber and the second chamber are separated by a breakable seal.

In any of the various embodiments discussed herein, the method may further include introducing a reconstituting solution into a second chamber of the flexible bag.

In any of the various embodiments discussed herein, the method may further include introducing a gas into the first chamber and sealing the first port after the pharmaceutical product in the first chamber has been lyophilized.

In any of the various embodiments discussed herein, the method may further include applying a predetermined amount of pressure to the flexible bag to break the breakable seal between the first chamber and the second chamber and mixing the reconstituting solution with the lyophilized pharmaceutical product in the first chamber to create a reconstituted pharmaceutical product.

In any of the various embodiments discussed herein, the method may further include administering the final pharmaceutical product to a patient through an administration port disposed in the flexible bag.

In any of the various embodiments discussed herein, the breakable seal is formed between the first chamber and the second chamber by joining a front surface of the flexible bag and the back surface of the flexible bag.

In any of the various embodiments discussed herein, the breakable seal comprises a weak point where the breakable seal is not as wide as the rest of the breakable seal and the breaking of the breakable seal initiates at the weak point when pressure is applied to the flexible bag.

In any of the various embodiments discussed herein, the pharmaceutical product is a cytotoxic drug.

In any of the various embodiments discussed herein, the cytotoxic drug is selected from the group consisting of: azacytidine, belinostat, bendamustine, brentuximab vedotin, bleomycin, bortezomib, busulfan, carboplatin, carmustine, cyclophosphamide, cytarabine, dacarbazine, dactinomycin, daunorubicin, decitabine, deferoxamine, doxorubicin, epirubicin hydrochloride, fludarabine, fotemustine, fulvestrant, gemcitabine, idarubicin, ifosfamide, irinotecan hydrochloride, ixabepilone, melphalan, methotrexate, oxaliplatin, paclitaxel, pemetrexed, pentostatin, raltitrexed, romidepsin, temozolomide, thiotepa, topotecan, trabectedin, trastuzumab, and vinblastine.

In any of the various embodiments discussed herein, the reconstituting solution is a 0.9% saline solution.

In any of the various embodiments discussed herein, the bag is fabricated from a polyolefine/styrene-block copolymer based film.

Some embodiments may include a flexible pharmaceutical bag that includes a first chamber configured to hold a lyophilized pharmaceutical product, a second chamber separated from the first chamber, the second chamber configured to hold a reconstituting solution for reconstituting the lyophilized pharmaceutical product in the first chamber, a seal disposed between the first chamber and the second chamber that separates and seals the first chamber from the second chamber and a first port attached to the first chamber, the first port configured to introduce a pharmaceutical product into the first chamber and allow passage of water vapor from the pharmaceutical product during lyophilization of the pharmaceutical product.

In any of the various embodiments discussed herein, the bag may further include a second port attached to the second chamber, the second port configured to introduce the reconstituting solution to the second chamber for reconstituting the lyophilized pharmaceutical product in the first chamber.

In any of the various embodiments discussed herein, the seal is a connection between a front surface of the pharmaceutical bag and a back surface of the pharmaceutical bag.

In any of the various embodiments discussed herein, the seal extends the length of the pharmaceutical bag between the first chamber and the second chamber.

In any of the various embodiments discussed herein, a predetermined amount of pressure applied to the pharmaceutical bag breaks the seal and connects the second chamber to the first chamber.

In any of the various embodiments discussed herein, the seal further comprises a weak point to provide an initial breaking point when a predetermined amount of pressure is applied to the pharmaceutical bag.

In any of the various embodiments discussed herein, the pharmaceutical product is a cytotoxic drug.

In any of the various embodiments discussed herein, the cytotoxic drug is selected from the group consisting of: azacytidine, belinostat, bendamustine, brentuximab vedotin, bleomycin, bortezomib, busulfan, carboplatin, carmustine, cyclophosphamide, cytarabine, dacarbazine, dactinomycin, daunorubicin, decitabine, deferoxamine, doxorubicin, epirubicin hydrochloride, fludarabine, fotemustine, fulvestrant, gemcitabine, idarubicin, ifosfamide, irinotecan hydrochloride, ixabepilone, melphalan, methotrexate, oxaliplatin, paclitaxel, pemetrexed, pentostatin, raltitrexed, romidepsin, temozolomide, thiotepa, topotecan, trabectedin, trastuzumab, and vinblastine.

In any of the various embodiments discussed herein, the reconstituting solution is a 0.9% saline solution.

In any of the various embodiments discussed herein, the pharmaceutical bag is fabricated from a polyolefine/styrene-block copolymer based film.

In any of the various embodiments discussed herein, the pharmaceutical bag withstands 121° Celsius.

In any of the various embodiments discussed herein, the pharmaceutical bag withstands −55° Celsius.

In any of the various embodiments discussed herein, the second chamber further comprises an administration port for administering a reconstituted pharmaceutical product that is a result of mixing the lyophilized pharmaceutical product and the reconstituting solution.

Some embodiments may include a flexible pharmaceutical bag may include a front film, a back film, an outer seal joining the front film to the back film around a perimeter of the pharmaceutical bag, and a breakable seal joining the front film and the back film interior of the outer seal, the breakable seal defining a first chamber and a second chamber separated from the first chamber. The first chamber is configured to hold a lyophilized pharmaceutical product, the second chamber is configured to hold a reconstituting solution for reconstituting the lyophilized pharmaceutical product in the first chamber, and the breakable seal breaks before the outer seal when a predetermined amount of pressure is applied to the flexible pharmaceutical bag.

In any of the various embodiments discussed herein, the first chamber and the second chamber are defined by the outer seal and the breakable seal.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of preparing a pharmaceutical product in a multiple chamber flexible bag, the method comprising:
   introducing the pharmaceutical product in a liquid state into a first chamber of the flexible bag through a first port; and
   lyophilizing the pharmaceutical product within the first chamber of the flexible bag to provide a lyophilized pharmaceutical product,
   wherein the flexible bag has a second chamber and a third chamber,
   wherein the first chamber and the second chamber are separated by a first breakable seal,
   wherein the third chamber is separated from one of the first and the second chambers by a second breakable seal, and
   wherein the pharmaceutical product is a cytotoxic drug.

2. The method according to claim 1, further comprising introducing a reconstituting solution into the second chamber of the flexible bag.

3. The method according to claim 2, wherein the reconstituting solution is a 0.9% saline solution.

4. The method according to claim 1, further comprising introducing a gas into the first chamber and sealing the first port after the pharmaceutical product in the first chamber has been lyophilized.

5. The method according to claim 1, further comprising applying a predetermined amount of pressure to the flexible bag to break the first breakable seal between the first chamber and the second chamber; and
   mixing a reconstituting solution with the lyophilized pharmaceutical product in the first chamber to create a reconstituted pharmaceutical product.

6. The method according to claim 5, further comprising administering the reconstituted pharmaceutical product to a patient through an administration port disposed in the flexible bag.

7. The method according to claim 1, wherein the first breakable seal is formed between the first chamber and the second chamber by joining a front surface of the flexible bag and a back surface of the flexible bag.

8. The method according to claim 7, wherein the first breakable seal comprises a weak point where the first breakable seal is not as wide as the rest of the first breakable seal, and
   wherein the breaking of the first breakable seal initiates at the weak point when pressure is applied to the flexible bag.

9. The method according to claim 1, wherein the pharmaceutical product is an antineoplastic or an immunomodulating agent.

10. The method according to claim 1, wherein the pharmaceutical product is selected from the group consisting of: azacytidine, belinostat, bendamustine, brentuximab vedotin, bleomycin, bortezomib, busulfan, carboplatin, carmustine, cyclophosphamide, cytarabine, dacarbazine, dactinomycin, daunorubicin, decitabine, deferoxamine, doxorubicin, epirubicin hydrochloride, fludarabine, fotemustine, fulvestrant, gemcitabine, idarubicin, ifosfamide, irinotecan hydrochloride, ixabepilone, melphalan, methotrexate, oxaliplatin, paclitaxel, pemetrexed, pentostatin, raltitrexed, romidepsin, temozolomide, thiotepa, topotecan, trabectedin, trastuzumab, and vinblastine.

11. The method according to claim 1, wherein the flexible bag is fabricated from a polyolefine/styrene-block copolymer based film.

\* \* \* \* \*